(12) United States Patent
Britton et al.

(10) Patent No.: US 7,590,932 B2
(45) Date of Patent: Sep. 15, 2009

(54) ELECTRONIC HEALTHCARE MANAGEMENT FORM CREATION

(75) Inventors: Catherine Britton, Dover, PA (US); Kiron Rao, Bangalore (IN); Terri H. Steinberg, West Chester, PA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 1120 days.

(21) Appl. No.: 10/383,324

(22) Filed: Mar. 7, 2003

(65) Prior Publication Data

US 2004/0015778 A1   Jan. 22, 2004

Related U.S. Application Data

(60) Provisional application No. 60/364,540, filed on Mar. 16, 2002.

(51) Int. Cl.
*G06F 17/00* (2006.01)
(52) U.S. Cl. .................. 715/222; 715/221; 715/235
(58) Field of Classification Search ......... 715/505–506, 715/221, 222, 235
See application file for complete search history.

(56) References Cited

U.S. PATENT DOCUMENTS 4,553,261 A   11/1985   Froessl (Continued)

FOREIGN PATENT DOCUMENTS

EP   0 544 432 A2   11/1992

(Continued)

OTHER PUBLICATIONS

HTML 4.01 Specification http://www.w3.org/TR/html4, Dec. 24, 1999.

(Continued)

*Primary Examiner*—Boris Pesin

(57) ABSTRACT

Certain exemplary embodiments of the present invention provide a method for creating an electronic form for use in healthcare management. The method can comprise initiating generation of at least one display image supporting a user in: selecting a template form from a repository of template forms; modifying said selected template form by linking a user selected object from a predetermined list of objects with a user selected data field of said selected template form, objects in said predetermined list being associated with at least one of, (a) a particular role of a healthcare worker and (b) a particular activity being performed in providing healthcare to a patient, said selected object being usable in determining a query to be used in soliciting data for entry in said user selected data field; and associating a name with said modified form. The method can also comprise storing said modified form in response to user command. It is emphasized that this abstract is provided to comply with the rules requiring an abstract that will allow a searcher or other reader to quickly ascertain the subject matter of the technical disclosure. This abstract is submitted with the understanding that it will not be used to interpret or limit the scope or meaning of the claims. 37 CFR 1.72(b).

24 Claims, 12 Drawing Sheets

U.S. PATENT DOCUMENTS

| | | | |
|---|---|---|---|
| 4,945,476 A | | 7/1990 | Bodick et al. |
| 5,159,667 A | | 10/1992 | Borrey |
| 5,164,899 A | | 11/1992 | Inn |
| 5,619,592 A | | 4/1997 | Bloomberg |
| 5,647,021 A | | 7/1997 | Fortune |
| 5,664,109 A | | 9/1997 | Campbell |
| 5,832,450 A | * | 11/1998 | Myers et al. .................. 705/3 |
| 5,924,074 A | * | 7/1999 | Evans ........................... 705/3 |
| 6,052,693 A | | 4/2000 | Hayward-shott |
| 6,084,585 A | * | 7/2000 | Kraft et al. ................. 715/733 |
| 6,266,682 B1 | | 7/2001 | Lamarca |
| 6,341,287 B1 | * | 1/2002 | Sziklai et al. ............... 707/102 |
| 6,668,253 B1 | * | 12/2003 | Thompson et al. ............ 707/10 |
| 2002/0082865 A1 | * | 6/2002 | Bianco et al. ................. 705/2 |
| 2002/0103673 A1 | * | 8/2002 | Atwood ......................... 705/2 |
| 2003/0078806 A1 | * | 4/2003 | Kudryk et al. ................. 705/2 |
| 2003/0208381 A1 | * | 11/2003 | Walter et al. .................. 705/3 |
| 2004/0008223 A1 | | 1/2004 | Britton et al. |
| 2004/0220829 A1 | * | 11/2004 | Baharav et al. ................ 705/2 |
| 2004/0254816 A1 | * | 12/2004 | Myers ........................... 705/2 |

FOREIGN PATENT DOCUMENTS

WO      WO 02/07091 A2      1/2002

OTHER PUBLICATIONS

PDF In-Depth a Steb-by-Step Introduction http://www.planetpdf.com/developer/article.asp?, Feb. 1, 2001.

13 Objects, Images, and Applets http://www.w3.org/TR/htm14/struct/objects.html.

\* cited by examiner

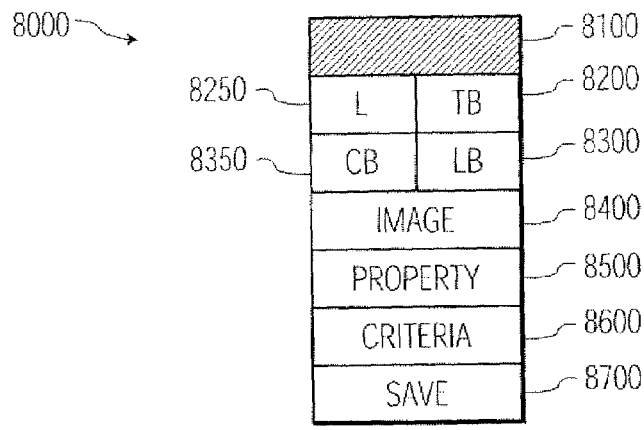
FIG. 8
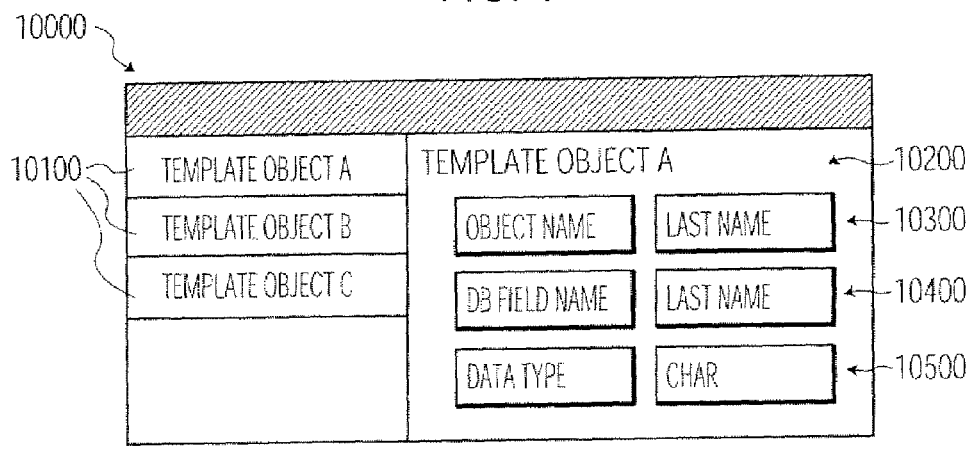
FIG. 9
FIG. 10

ELECTRONIC HEALTHCARE MANAGEMENT FORM CREATION

This application claims priority to pending provisional U.S. patent application Ser. No. 60/364,540, titled "Cardiology Form Builder and Display Tool," filed Mar. 16, 2002, now abandoned. This application is related to concurrently filed co-pending application, entitled "Electronic Healthcare Management Form Navigation," Ser. No. 10/383,299.

BACKGROUND

Computer systems have been employed to better manage the delivery of healthcare to patients, documentation of recommended and provided healthcare, billing for healthcare services, etc. Yet all too often, the user interfaces for such healthcare computer systems suffer from poor design, requiring users to abandon familiarity with paper-based forms and learn new layouts for data entry. Moreover, traditional computer-based layouts frequently do not reflect detailed understanding of the healthcare workflow, and can be difficult to re-design when healthcare workflow patterns change. Such misunderstandings of workflows can result in duplication of data, requiring more storage space than optimally required. Further, traditional computer-based layouts frequently prove difficult to navigate, particularly for navigating between features of various anatomical systems. Such sub-optimal navigational aspects can needlessly waste network and/or processor bandwidth when users navigate incorrectly between layouts.

SUMMARY

Certain exemplary embodiments of the present invention provide a method for creating an electronic form for use in healthcare management. The method can comprise initiating generation of at least one display image supporting a user in: selecting a template form from a repository of template forms; modifying said selected template form by linking a user selected object from a predetermined list of objects with a user selected data field of said selected template form, objects in said predetermined list being associated with at least one of, (a) a particular role of a healthcare worker and (b) a particular activity being performed in providing healthcare to a patient, said selected object being usable in determining a query to be used in soliciting data for entry in said user selected data field; and associating a name with said modified form. The method can also comprise storing said modified form in response to user command.

BRIEF DESCRIPTION OF THE DRAWINGS

The invention and its wide variety of potential embodiments will be readily understood via the following detailed description of certain exemplary embodiments, with reference to the accompanying drawings in which:

FIG. 8 is a diagram of an exemplary embodiment of a user interface 8000 of the present invention;

FIG. 9 is a diagram of an exemplary embodiment of a user interface 9000 of the present invention;

FIG. 10 is a diagram of an exemplary embodiment of a user interface 10000 of the present invention;

DETAILED DESCRIPTION

Figure 1:
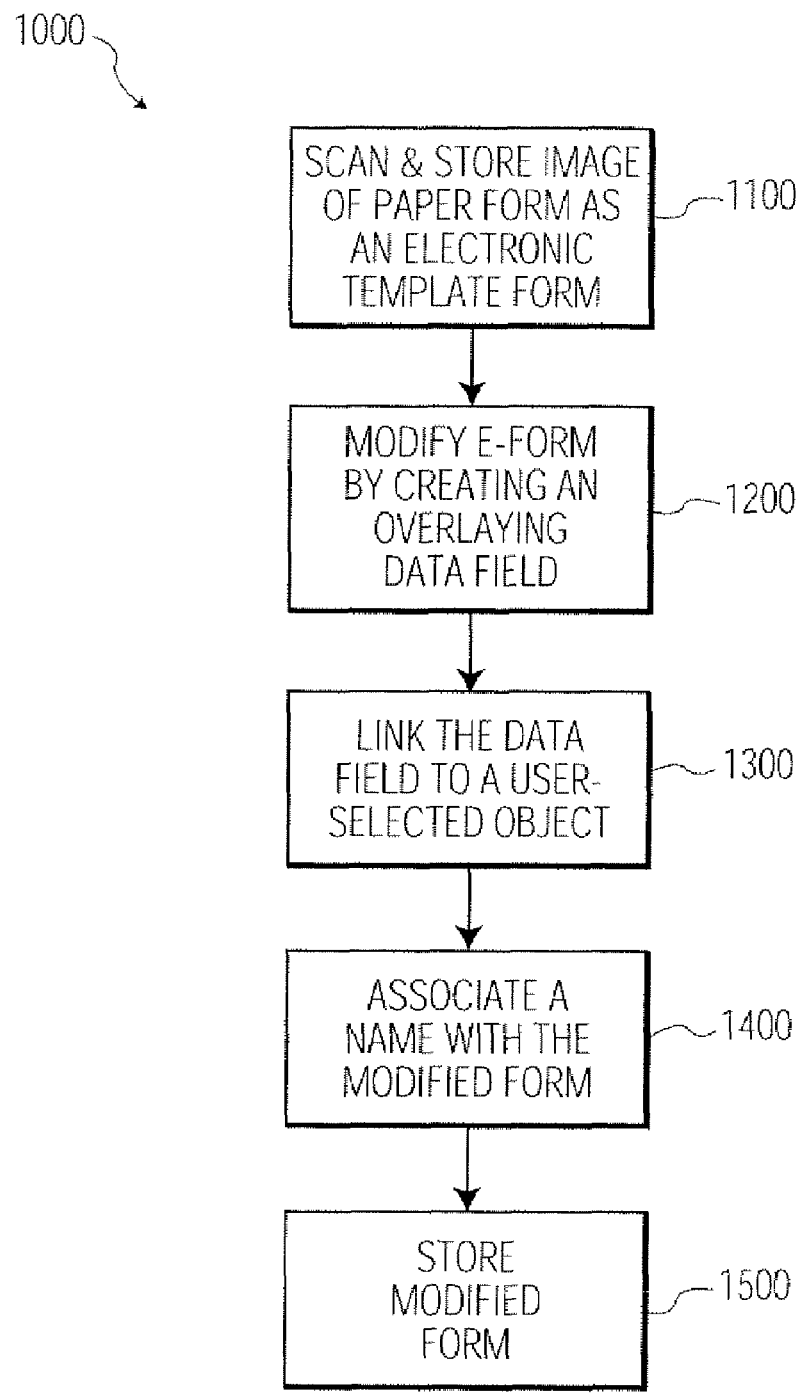
FIG. 1 is a flow diagram of an exemplary embodiment of a method 1000 of the present invention.

FIG. 1 is a flow diagram of an exemplary embodiment of a method 1000 of the present invention. Note that although various activities are presented in a numbered sequence, and are connected with arrows to an exemplary embodiment of method 1000, there is no general requirement that the activities be performed in any particular order or any particular number of times, or that all activities be performed. Moreover, any activity can be performed automatically and/or manually. Also, any activity can be combined and/or performed in conjunction with any activity of any other method described herein.

At activity 1100, a traditional paper form, such as any paper form commonly used in healthcare management, may be scanned. Once generated via the scanning process, the resulting image may be stored as an electronic template form in a repository of forms.

At activity 1200, a particular template form from a plurality of template forms in a forms repository may be selected and an image representing the template form may be rendered (as used herein, the word "rendered" means made perceptible to a human, via for example any visual and/or audio means, such as via a display, a monitor, electric paper, an ocular implant, a speaker, a cochlear implant, etc.). A user may then modify the form by selecting a portion of the form that is of interest, and creating an template data field that may appear to overlay or underlay the portion of interest. For example, via a graphical user interface, a user may create a template data field called "telephone number" by using a selection tool to draw and/or define a selection rectangle having borders that at least roughly correspond to the borders of a telephone number "box" that is part of the apparently underlying image.

At activity 1300, the template form may be modified by linking a selected template data field, such as the field created in the preceding paragraph, to a user-selected object. The object may be selected from a list of objects. The list of objects may be created beforehand. In creating an object, a user may select a related object from the list and modify that related object to reflect the attributes of the desired object, then name and save the desired object, such that the name of the desired object is displayed along with the names of other objects when the list of objects is rendered. A saved object may be saved to a local directory and/or database and/or to a remote directory and/or database, such as a drive and/or database connected via a network, such as the Internet, an intranet, a public switched network, a private network, etc. A link to the saved object may be any form of link, such as a hyperlink and/or URL.

In certain embodiments, the list of objects may be categorized and/or may present a particular category of objects. For example, the list may be associated with a particular role and/or title of a healthcare worker, such as "Admissions Administrator" or "Cardiac Care Nurse". As another example, the list may be associated with a particular activity to be performed in providing healthcare to a patient, such as for example, admitting the patient to a healthcare facility, or fulfilling a laboratory testing request for the patient, or administering medication to the patient. Thus, an object may be assigned to a category representing, for example, a worker role, worker title, and/or healthcare activity, etc., and the list may reflect that category and/or categorization.

In certain embodiments, the user-selected object may be created by selecting a name, data type, data length, and/or action for the object, etc. Once created, the object may be saved. The object may be related to other items in the list before, during, and/or after creation of the object.

In certain embodiments, the user-selected object may be usable for entering data into a database. For example, a template data field labeled "home telephone number" may be linked to a field in a patient database for home telephone number. Thus, data entered for the template data field via the template form may be transferred to one or more databases, potentially depending on a particular role and/or title of a healthcare worker, and/or a particular activity that has been or will be performed in providing healthcare to a patient.

In certain embodiments, the user-selected object may be usable for determining a query to be used for soliciting data for entry in the user selected data field. For example, in a data field called "home telephone number", a query may be rendered indicating "What is the patient's home telephone number, including area code?" As another example, in a data field called "patient oral temperature", a query may be rendered indicating "What is the patient's oral temperature, in degrees Fahrenheit?" In certain embodiments, the user-selected object may be useable for forming a query of data associated with the user selected data field.

At activity 1400, a name may be associated with the modified form, such as for example, "New Patient Admission Form" or "Medication Administration Record". In certain embodiments, the name may be suggested to a user. In certain embodiments, the user may provide the name. At activity 1500, in response to a user command, the modified form may be stored in the forms repository.

In certain embodiments, when a user selects the modified form, the form may be associated with a particular patient and/or a particular healthcare worker. Thus, for example, if the identity of the patient is known, the form may be at least partially pre-populated with data regarding the patient when the form is selected. Similarly, if the identity of the healthcare worker is known, the form may be at least partially pre-populated with data regarding the healthcare worker. Alternatively, if the identity of the patient and/or healthcare worker becomes known after opening of the form, the form may be at least partially populated, as appropriate, with data regarding that person.

Figure 2:
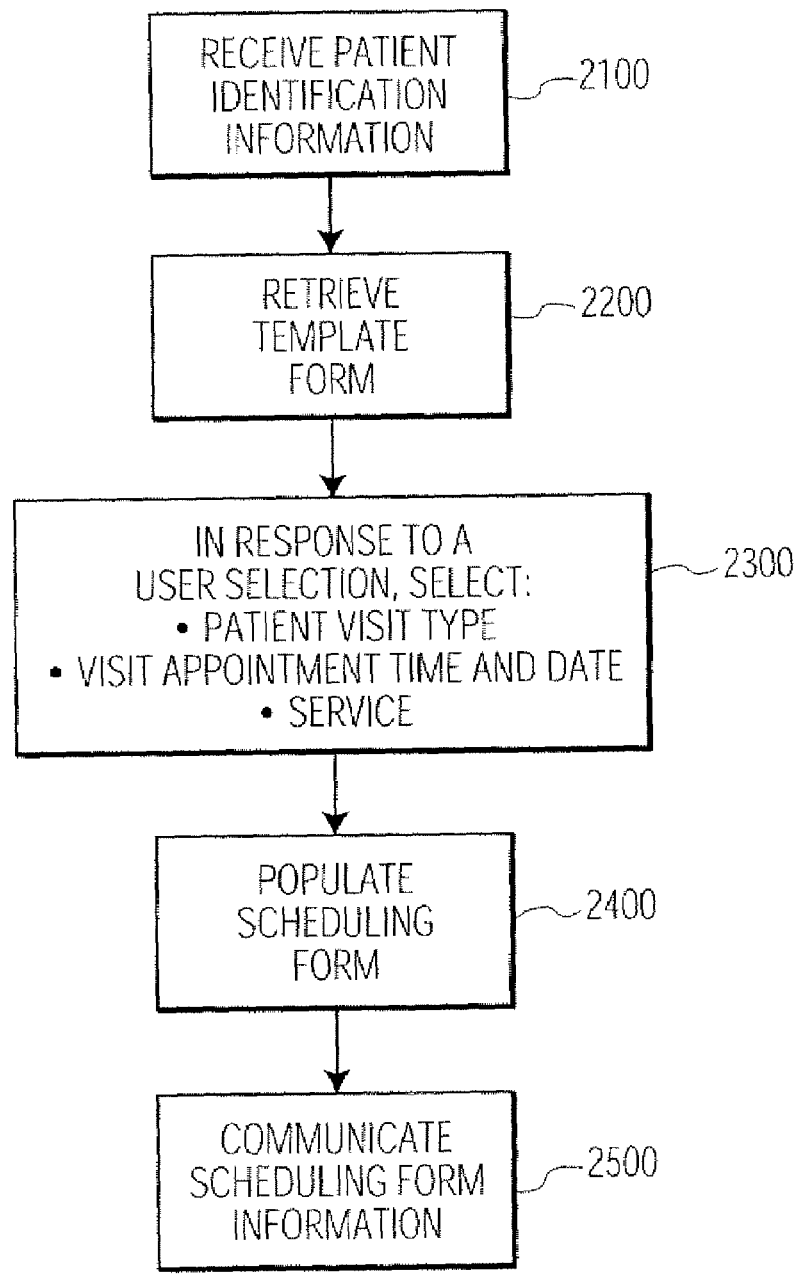
FIG. 2 is a flow diagram of an exemplary embodiment of a method 2000 of the present invention.

FIG. 2 is a flow diagram of an exemplary embodiment of a method 2000 of the present invention. Note that although various activities are presented in a numbered sequence, and are connected with arrows to an exemplary embodiment of method 2000, there is no general requirement that the activities be performed in any particular order or any particular number of times, or that all activities be performed. Moreover, any activity may be performed automatically and/or manually. Also, any activity may be combined and/or performed in conjunction with any activity of any other method described herein.

At activity 2100, patient information may be received. Such information may be received via any means, including for example, keyboard entry, voice-entry, selection from a list of patients, push technology, activation of a hyperlink contained in an e-mail message, etc.

At activity 2200, a template form may be retrieved for scheduling a visit. The template form may be user-selected via for example a graphical user interface, and/or associated with a visit scheduling activity and/or object.

At activity 2300, in response to a user selection, a patient visit type, a visit appointment date and time, a service, and/or an activity may be selected. For example, via for example a graphical user interface, a patient visit type may be selected from a list including, for example: routine physical, lab work, testing, counseling, out-patient procedure, etc. A visit appointment date and time may be selected from a graphical user interface resembling, for example, a calendar and/or clock. Services and/or activities may be selected from a list including, for example: measure blood pressure, measure weight, draw blood sample, provide exercise counseling, etc.

At activity 2400, a scheduling form may be populated with the obtained and/or selected information, such as the patient identification information, patient visit type, visit appointment date and time, service, and/or activity.

At activity 2500, the populated scheduling form may be communicated to a recipient application to enable a user of that application to schedule a patient visit, via for example a graphical user interface.

Figure 3:
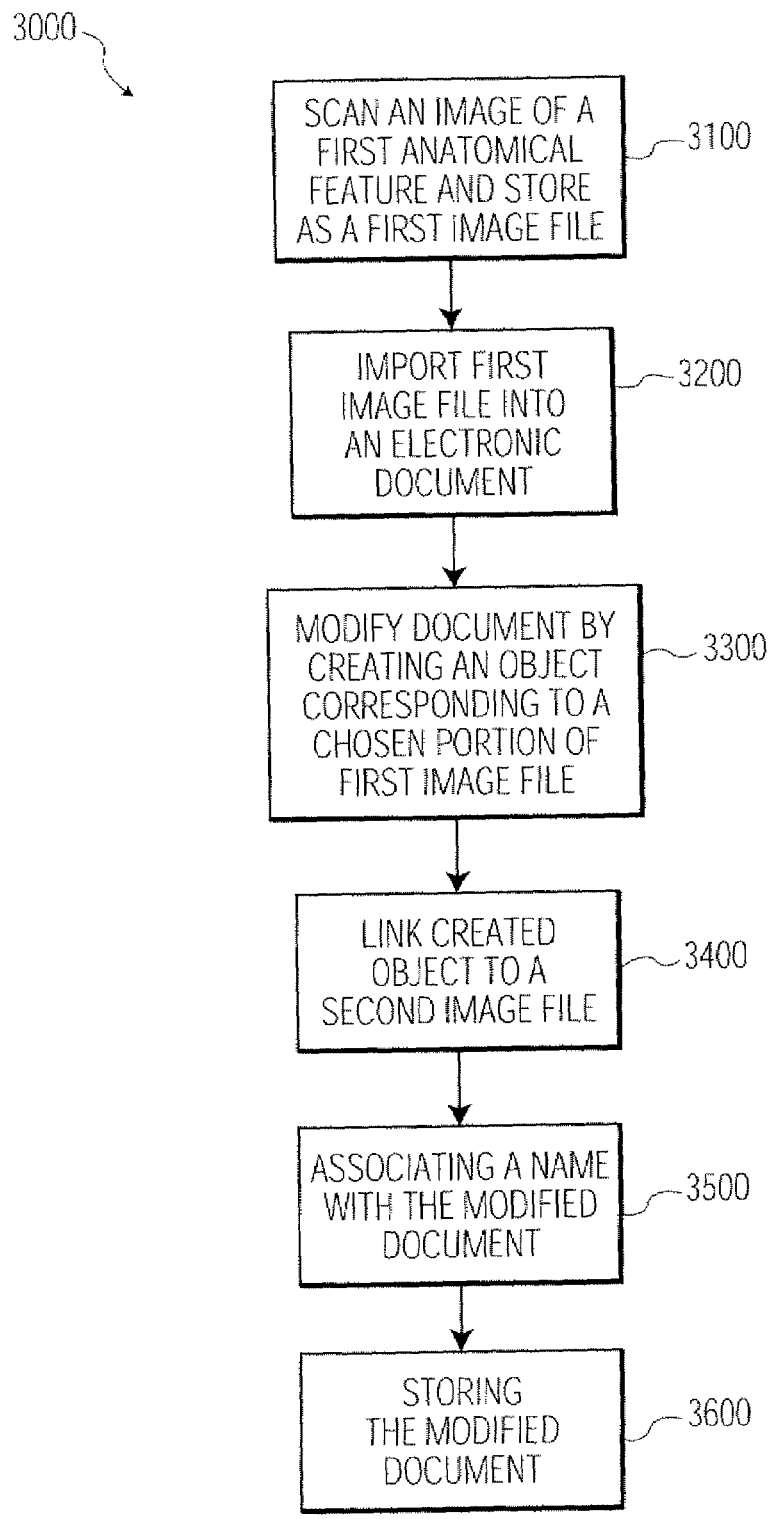
FIG. 3 is a flow diagram of an exemplary embodiment of a method 3000 of the present invention.

FIG. 3 is a flow diagram of an exemplary embodiment of a method 3000 of the present invention. Note that although various activities are presented in a numbered sequence, and are connected with arrows to an exemplary embodiment of method 3000, there is no general requirement that the activities be performed in any particular order or any particular number of times, or that all activities be performed. Moreover, any activity may be performed automatically and/or manually. Also, any activity may be combined and/or performed in conjunction with any activity of any other method described herein.

At activity 3100, a image of a first anatomical feature, such as that found in an anatomy treatise or textbook, may be scanned. For example, the first anatomical feature could be a human heart. Once generated via the scanning process, the resulting image may be stored as a first electronic image file in repository of such image files. Alternatively, the first electronic image file may be generated via obtaining clip art of the desired first anatomical feature.

At activity 3200, the first image file may be imported into an electronic document, such as via a "copy" and "paste" routine. Alternatively, the first image file itself may be utilized as the electronic document.

At activity 3300, via for example a graphical user interface, the electronic document may be modified by decomposing the image of the anatomical feature into a plurality of segments, portions, and/or views of the anatomical feature, such as via creating an object corresponding to a chosen segment, portion, and/or view. For example, if the anatomical feature is a human body, a portion of the body, such as the heart, could be selected by using a selection tool to draw and/or define a selection polygon and/or shape having borders that at least roughly correspond to the borders of the heart as visible in the apparently underlying image of the human body. The pixels and/or locations within the borders could correspond to locations a user might click and/or select to activate display of a linked object, such as a linked graphic image of the selected portion of the anatomical feature. The bordered region may be named, grouped with other bordered regions, browsed, mapped to a database element, and/or have its own linked image.

As another example, if the anatomical feature is an arterial system and/or subsystem, such as the arteries serving the heart muscle itself, various arterial segments may be selected and assigned a corresponding object. Thus, an object may be assigned to, for example, the mid LAD or to the distal RCA. An object may inherit characteristics from a neighboring segment object. Thus, assuming a segment object has already been defined for the upper distal RCA, characteristics of that object may be provided to a newly created object for the middle distal RCA.

At activity 3400, via for example a graphical user interface, the object associated with the portion and/or view of the first image may be linked to a second image file, to enable navigation from the first image to the second image. For example, via one or more lists and/or pop-up menus of objects representing human body parts, organs, views, and/or systems, and/or heart components, views, and/or subsystems, the object corresponding to the human body may be linked to a detailed image of a heart to enable a user to navigate to the detailed image by clicking on the image of the human body in the vicinity of the heart.

Thus, the second image could be considered a child of the parent first image. Any parent may have multiple children. Any child may be associated with multiple parents. Any child may specify a parent from which the child inherits one or more attributes and/or properties, such as a window size within which the image is displayed, font for any corresponding text, etc. Likewise, a parent may specify default properties for its children. In certain embodiments, a child may override such default properties. In certain embodiments, a child may not override such default properties.

In certain embodiments, the first image may render indicators of those regions to which objects are associated and/or second images are linked. Such indicators may be rendered as hot spots, mouse-overs, and/or a list of regions. For example, a user may click on an icon and/or press a particular keyboard combination and all linked regions will be displayed with bright red borders. As another example, a user may move a pointer over a region and its border will be displayed in red, and/or a textual label for the region will appear, and/or an address and/or name of the image to which the region is associated will be displayed.

In certain embodiments, a child may render indicators of each parent with which it is associated. In certain embodiments, a child may render an indicator of one or more branches of its family tree. That is, if the child was rendered as a result of navigation from a grandparent image to a parent image to the child image, that navigational path may be rendered. Potentially, the rendering of the navigational path may include a hyperlink associated with each image in the path to enable rapid return to an image of interest. Conversely, any image may include a display of its descendants to any desired number of generations, thereby enabling rapid navigation to a particular descendant of interest, such as a great-grandchild image. Such a display of descendants may be in the form of a tree having branches with names for the corresponding descendant and/or miniature previews of each descendant.

At activity 3500, a name may be associated with the modified electronic document that comprises the object linked to the second image file. At activity 3600, the modified electronic document may be stored. In certain embodiments, portions of the modified electronic document may be named and/or stored. For example, a user may specify that only the graphical aspects of an electronic document are to be stored in a file of a particular name. As another example, a user may specify the storage of only the textual aspects of an electronic document. As another example, a user may specify the storage of both the graphical and textual aspects of an electronic document, but without any objects that link to databases and/or other documents. In certain embodiments, a miniature preview of the electronic document may be named and/or stored, either individually and/or combined with any portion of the electronic document, including the entire electronic document.

In certain embodiments, the created and/or modified documentation may be associated with, for example, a particular patient, a particular healthcare activity, a particular procedure, and/or a particular healthcare worker. In certain embodiments, data related to the associated patient, healthcare activity, procedure, and/or healthcare worker may be included in the document.

In certain embodiments, activities 3300 through 3400 may be repeated for additional segment, portions, and/or views of the first anatomical feature. Thus, for example, various portions of the first anatomical feature may be linked to detailed views of, for example, the head, brain, digestive tract, lungs, urinary tract, blood vessels, etc.

In certain embodiments, activities 3100 through 3600 may be repeated using the second image file as a starting point. For example, an electronic document providing an image of the human heart may have associated navigable objects, each linking a different portion of the image of the heart (such as the ventricles, arteries, veins, etc.) to a detailed image of that portion. Such a detailed image may be more than merely a magnification of the parent image. Instead, it may contain additional detail and/or objects not found in the parent image.

Thus, a user who views for example, the first electronic document displaying the image of the human body may navigate to a detailed image of the heart by clicking in the vicinity of the heart. When the detailed image of the heart is rendered, the user may click in the region of the left ventricle to cause a detailed image of the left ventricle to be rendered. Thus, embodiments of method 3000 may provide customizable interactive graphical documents.

In certain embodiments, the object may be linked and/or associated with an element of one or more databases, such as a field of a database. For example, clicking on a predetermined location and/or area of a graphical image may generate one or more queries to a database and potentially return data contained within one or more fields of the database. In certain embodiments, the object may be defined such that selecting a particular location and/or area of a graphical image, such as via clicking, may allow and/or cause entry of data into a corresponding field of one or more databases. Data entry may occur via any means, including keying, clicking, gesturing, speaking, etc. Data entry may be implied via the nature of the defined object and/or a sequence of preceding events.

In certain embodiments, the object may be linked and/or associated with a location in an electronic document. For example, clicking on a predetermined location and/or area of a graphical image may cause an electronic document to open and/or a predetermined portion of, the electronic document to be rendered. For instance, clicking on an image of a left ventricle in an image of a human heart could cause one or more paragraphs from a treatise, report, or paper relating to the left ventricle to be displayed. In certain embodiments, a list of treatises, reports, and/or papers containing such paragraphs could be rendered, enabling the user to select the desired source for display.

In certain embodiments, textual information corresponding to the displayed anatomical feature may be rendered. For example, textual information associated with the heart may be displayed when an image of the heart is displayed. Such information may describe the names of various regions of the heart, measurements, data, conditions, observations, diagnosis, recommendations, treatment plan, surgical plan, intervention plan, and/or prognosis relating to a particular patient's heart, heart regions, and/or heart systems.

In various embodiments, the textual information may be rendered within, over, near, and/or next to the graphical image. In certain embodiments, the textual information may be rendered independently of the graphical information, such as in a separate window that may be opened and closed while viewing the electronic document containing the image.

In certain embodiments, graphical images may appear to overlay other graphical images. For instance, a graphical image showing an arterial view of the heart may include an image of a stent that has been prescribed and/or implanted as an intervention for a stenosis condition. Either displayed with the arterial view, or by clicking on image of the stent included in the arterial view, textual information regarding the stent may be rendered, such as for example, its dimensions, materials, features, manufacturer, brand, style, item number, implantation technique, date of implantation, implantation location, current location, etc.

In certain embodiments, a graphical user interface providing various tools may be provided for drawing and/or placing various shapes and/or images such that they appear over the apparently underlying image file. For example, when an image of the arterial system of the heart is rendered, a toolbox containing various types of stent objects may also be displayed, allowing the viewer to place an object comprising an image of a stent over an appropriate location of the arterial image. The stent may be anchored to one or more particular locations in the underlying image. For example, both ends of the stent may be anchored to desired locations in the underlying artery.

Continuing with the stent example, in certain embodiments, the exemplary stent object may be linked to various textual data regarding the stent. For example, upon selecting a stent object from the toolbox, a user may be queried for the type and/or manufacturer of the desired stent by presenting a list of stent types and/or manufacturers. In certain embodiments, the user may specify as much or as little information about the stent as is appropriate for the particular situation, with the option to specify additional and/or different information at a later time.

In certain embodiments, the selection of an object, such as the stent, may be linked to one or more databases, such as a supplies inventory database. Thus, selection of an object may potentially indicate that one or more physical objects corresponding to the selected electronic object have been used, consumed, and/or removed from inventory, potentially triggering re-ordering of the physical object to restore the inventory. Similarly, selection of an object may indicate that certain procedures may and/or will be performed, thereby potentially defining certain physical tasks to be performed. For example, selection of a stent may indicate that the stent was implanted, implying that various surgical tools were utilized, and implying that those surgical tools should be expected to soon arrive at a cleaning facility for sterilization. Such information may guide management of activities at the cleaning facility.

Depending on and/or corresponding to the displayed anatomical feature, other objects may be provided on a palette or toolbox, for augmenting the underlying image to better reflect a particular patient's situation. Such objects may include anatomical variations (e.g., tilted bladder, enlarged ventricle, muscular atrophy, osteoporosis, etc.), anatomical injuries (e.g., a collapsed lung, broken bone, torn miniscus, scar tissue, etc.), anatomical diseases (e.g., cirrhosis, ulcer, clogged artery, etc.), and/or surgical and/or diagnosis techniques (e.g., an appendectomy, laparoscopy, endoscopy, etc.). For example, an object may be selected that overlays an image of a colon with attached normal appendix with an image of a colon with an inflamed appendix. As another example, an object may be selected that overlays an image of a colon with attached normal appendix with an image of a colon with a removed appendix. As yet another example, an object may be selected that provides an image of an endoscope that may be manipulated to correspond to the contours of an underlying colon.

Figure 4:
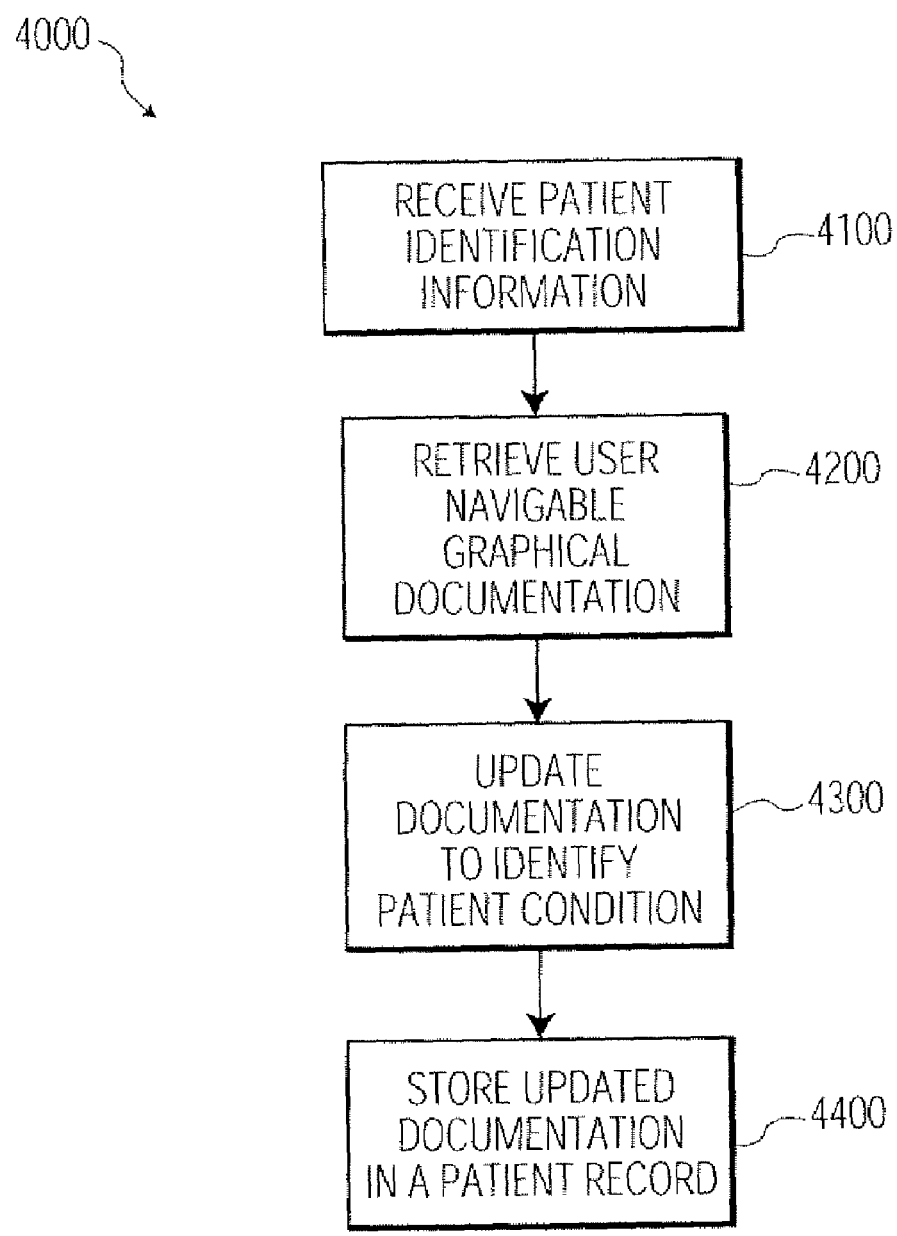
FIG. 4 is a flow diagram of an exemplary embodiment of a method 4000 of the present invention.

FIG. 4 is a flow diagram of an exemplary embodiment of a method 4000 of the present invention. Note that although various activities are presented in a numbered sequence, and are connected with arrows to an exemplary embodiment of method 4000, there is no general requirement that the activities be performed in any particular order or any particular number of times, or that all activities be performed. Moreover, any activity may be performed automatically and/or manually. Also, any activity may be combined and/or performed in conjunction with any activity of any other method described herein.

At activity 4100, patient identification information may be received by a user, and entered into a computer interface, such as a graphical user interface. Alternatively, the patient identification information may be received by a computer system.

At activity 4200, user navigable graphical documentation may be retrieved and rendered to a user. Such documentation may be created using any appropriate method, including method 3000.

At activity 4300, via for example a graphical user interface, the user navigable graphical documentation may be updated to reflect a patient condition, including measurements, data, observations, diagnoses, recommendations, treatment plans, surgical plans, intervention plans, and/or prognoses. In certain embodiments, the documentation may include data related to a particular healthcare activity, a particular procedure, and/or a particular healthcare worker.

At activity 4400, upon user command and/or automatically, the updated documentation may be stored in association with the patient's medical records.

Figure 5:
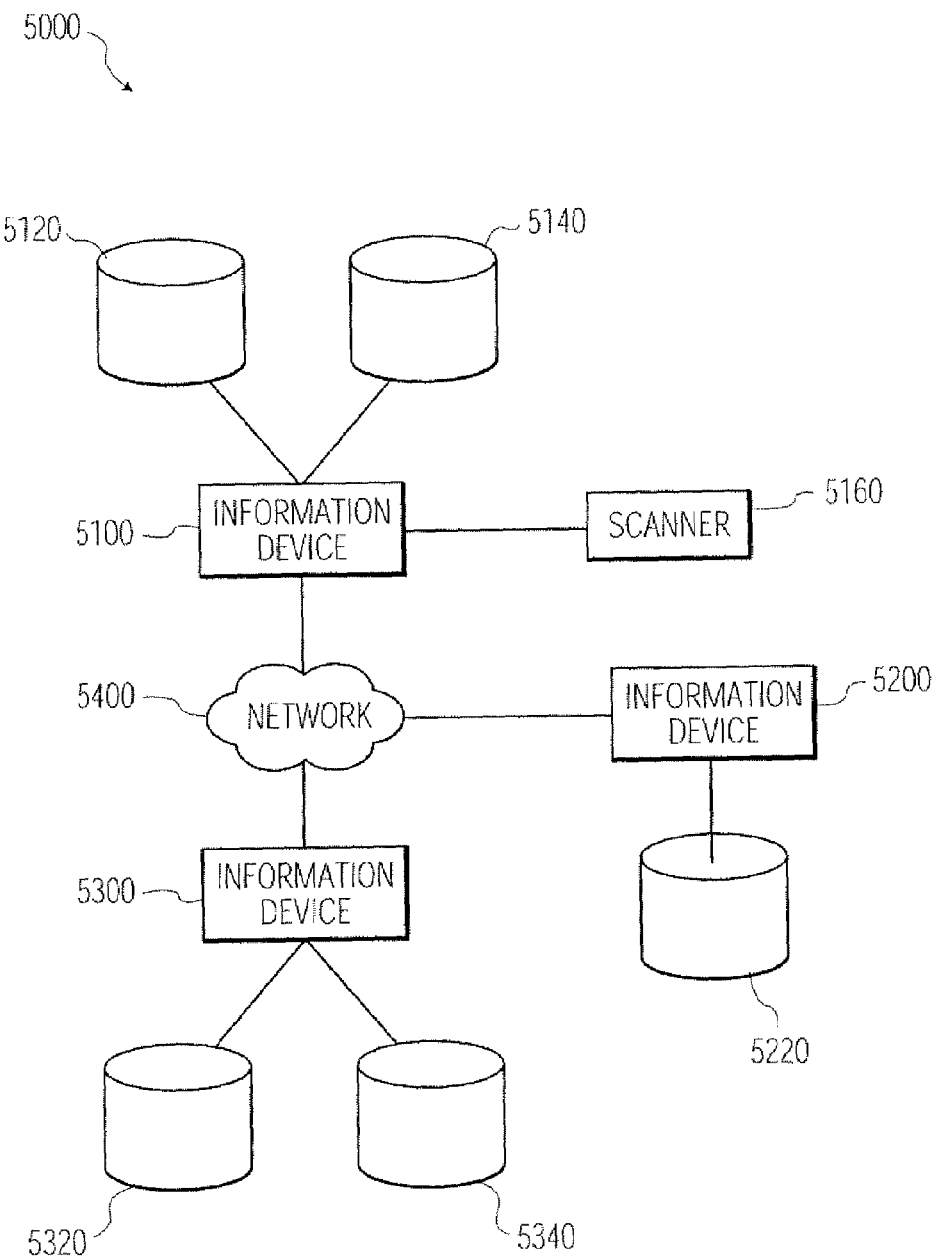
FIG. 5 is a block diagram of an exemplary embodiment of a system 5000 of the present invention.

FIG. 5 is a block diagram of an exemplary embodiment of a system 5000 of the present invention. As an initial matter, it suffices to say that, using the description of any of methods 1000, 2000, 3000, and/or 4000, one of ordinary skill in the art may implement the functionality of any of methods 1000, 2000, 3000, and/or 4000 via system 5000 utilizing any of a wide variety of well-known architectures, hardware, protocols, and/or software. Thus, the following description of system 5000 may be viewed as illustrative, and unless specified otherwise, should not be construed to limit the implementation of any of methods 1000, 2000, 3000, and/or 4000, and/or the scope of any claims attached hereto.

System 5000 may comprise one or more information devices 5100, 5200, 5300 inter-connected via a network 5400. Any of information devices 5100, 5200, 5300 may have any number of databases coupled thereto. For example, information device 5100 may be coupled to and/or host databases 5120 and 5140, information device 5200 may be coupled to and/or host database 5220, and/or information device 5300 may be coupled to and/or host databases 5320 and 5340. Moreover, any information device may act as a bridge, gateway, and/or server of its databases to any other information device. Thus, for example, information device 5100 may access database 5320 via information device 5300.

A scanner 5160 may be coupled to any of information devices 5100, 5200, 5300. Network 5400 may be any type of communications network, including, for example, a packet switched, connectionless, IP, Internet, intranet, LAN, WAN, connection-oriented, switched, and/or telephone network.

Figure 6:
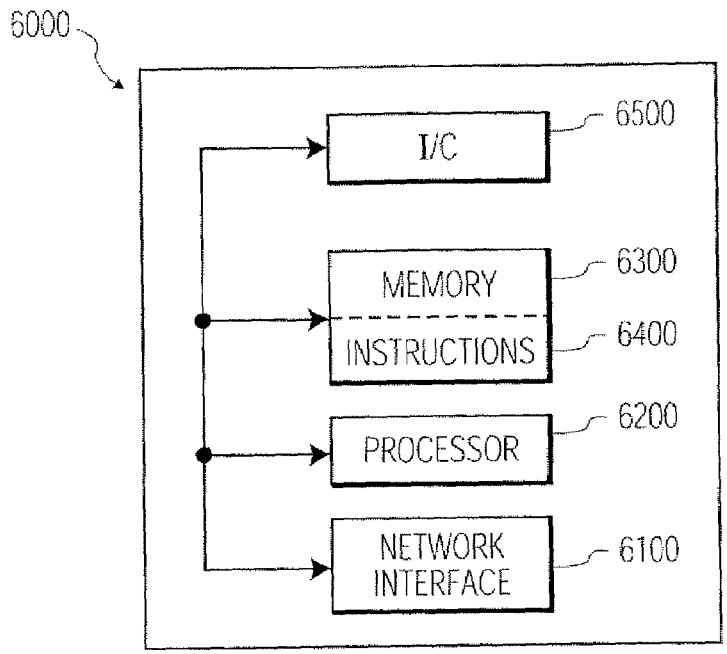
FIG. 6 is a block diagram of an exemplary embodiment of an information device 6000 of the present invention.

FIG. 6 is a block diagram of an exemplary embodiment of an information device 6000 of the present invention. Information device 6000 may represent any of information devices 5100, 5200, 5300 of FIG. 5. In certain embodiments, information device 6000 may be implemented on a general purpose or special purpose computer, such as a personal computer, workstation, server, minicomputer, mainframe, supercomputer, laptop, and/or Personal Digital Assistant (PDA), etc., a programmed microprocessor or microcontroller and/or peripheral integrated circuit elements, an ASIC or other integrated circuit, a hardware electronic logic circuit such as a discrete element circuit, and/or a programmable logic device such as a PLD, PLA, FPGA, or PAL, or the like, etc. In general any device on which resides a finite state machine capable of implementing at least a portion of a method described herein may be used for information device 6000.

Information device 6000 may include well-known components such as one or more communication interfaces 6100, one or more processors 6200, one or more memories 6300 containing instructions 6400, and/or one or more input/output (I/O) devices 6500, etc.

In various embodiments, communication interface 6100 may be and/or include a bus, connector, network adapter, wireless network interface, wired network interface, modem, radio receiver, transceiver, and/or antenna, etc.

Each processor 6200 may be a commercially available general-purpose microprocessor. In certain embodiments, the processor may be an Application Specific Integrated Circuit (ASIC) or a Field Programmable Gate Array (FPGA) that has been designed to implement in its hardware and/or firmware at least a part of a method in accordance with an embodiment of the present invention.

Memory 6300 may be coupled to processor 6200 and may comprise any device capable of storing analog or digital information, such as a hard disk, Random Access Memory (RAM), Read Only Memory (ROM), flash memory, a compact disk, a digital versatile disk (DVD), a magnetic tape, a floppy disk, and any combination thereof. Memory 6300 may also comprise a database, an archive, and/or any stored data and/or instructions. For example, memory 6300 may store instructions 6400 adapted to be executed by processor 6200 according to one or more activities of a method of the present invention.

Instructions 6400 may be embodied in software, which may take any of numerous forms that are well known in the art, including for example, Visual Basic by Microsoft Corporation of Redmond, Wash. Instructions 6400 may control operation of information device 6000 and/or one or more other devices, systems, or subsystems coupled thereto.

I/O device 6500 may be an audio and/or visual device, including, for example, a monitor, display, indicator, light, keyboard, keypad, touchpad, pointing device, microphone, speaker, telephone, fax, video camera, camera, scanner, and/or printer, including a port to which an I/O device may be attached, connected, and/or coupled.

Figure 7:
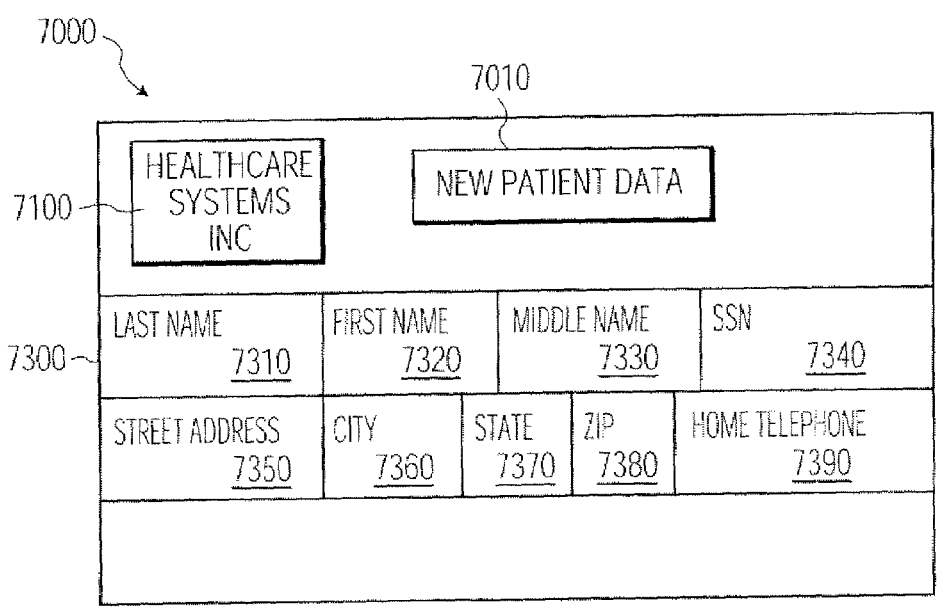
FIG. 7 is a diagram of an exemplary embodiment of a user interface 7000 of the present invention.

FIG. 7 is a diagram of an exemplary embodiment of a user interface 7000 of the present invention. User interface 7000 may render an image 7010 of a scanned healthcare form, such as a new patient data form that might be used for creating a medical record file for a new patient, and/or for admitting a new patient. Image 7010 might include a logo 7100 of the healthcare provider, a title for the form, and various fields 7300, such as fields for last name 7310, first name 7320, middle name 7330, social security number 7340, street address 7350, city 7360, state 7370, zip code 7380, and/or home telephone number 7390.

FIG. 8 is a diagram of an exemplary embodiment of a user interface 8000 of the present invention. User interface 8000 may render an image of a toolbox, window, or palette 8100, that may include various tools or controls for creating, specifying, and/or manipulating objects to be associated with an electronic document that includes image 7010 of FIG. 7. Such controls may include tools for creating a label (L) 8250, text box (TB) 8200, combo box (CB) 8350, list box (LB) 8300, linked image 8400, object property 8500, and/or object criteria 8600. A save tool 8700 may also be provided for commanding that a document be saved.

To create a template, a user can, for example, select "New Template" from a "Template" menu. From toolbox 8100, the user may click on a desired control and drag it into position on the new template to add that control to the new template.

The user may change properties of the selected control and/or the template as desired. For example, a user may specify an appearance, background color, background style, border style, foreground color, font, font style, font size, alignment, line spacing, indent, maximum data length, validation, query, cursor type, pointer type, autosizing, position, and/or dimension, etc. for a control. A control may be associated with a database field. Data entry via the control may be prompted by a query. Data entry via the control may be validated. Searches of the database may be performed using one or more queries entered via one or more controls.

As another example, a user may specify a name, start-up behavior, access control, password, window type, window position, horizontal dimension, vertical dimension, data entry order, tab order, page breaks, header, footer, etc. for the template.

A template may be associated with a category and/or group of templates. For example, an EKG template may be associated with a category, group, folder, and/or sub-directory of cardiology templates. Via for example a template browser, templates may be moved from one category and/or group to another, opened, renamed, modified, and/or deleted. Moreover, via for example a template brower, access control for one or more templates and/or groups of templates may be specified.

FIG. 9 is a diagram of an exemplary embodiment of a user interface 9000 of the present invention. User interface 9000 may display an object, such as template object A 9100 that has been created using a control from toolbox 8100 of FIG. 8 "over" a scanned form image 7010 of FIG. 7.

FIG. 10 is a diagram of an exemplary embodiment of a user interface 10000 of the present invention. User interface 10000 may display a list of objects 10100, such as template objects A, B, and C. Moreover, user interface 10000 may display information 10200 regarding an object selected from list 10100, such as the object name 10300, an associated database field 10400, and/or a data type 10500 (e.g., character, variable-length character, integer, and/or boolean, etc.).

Figure 11:
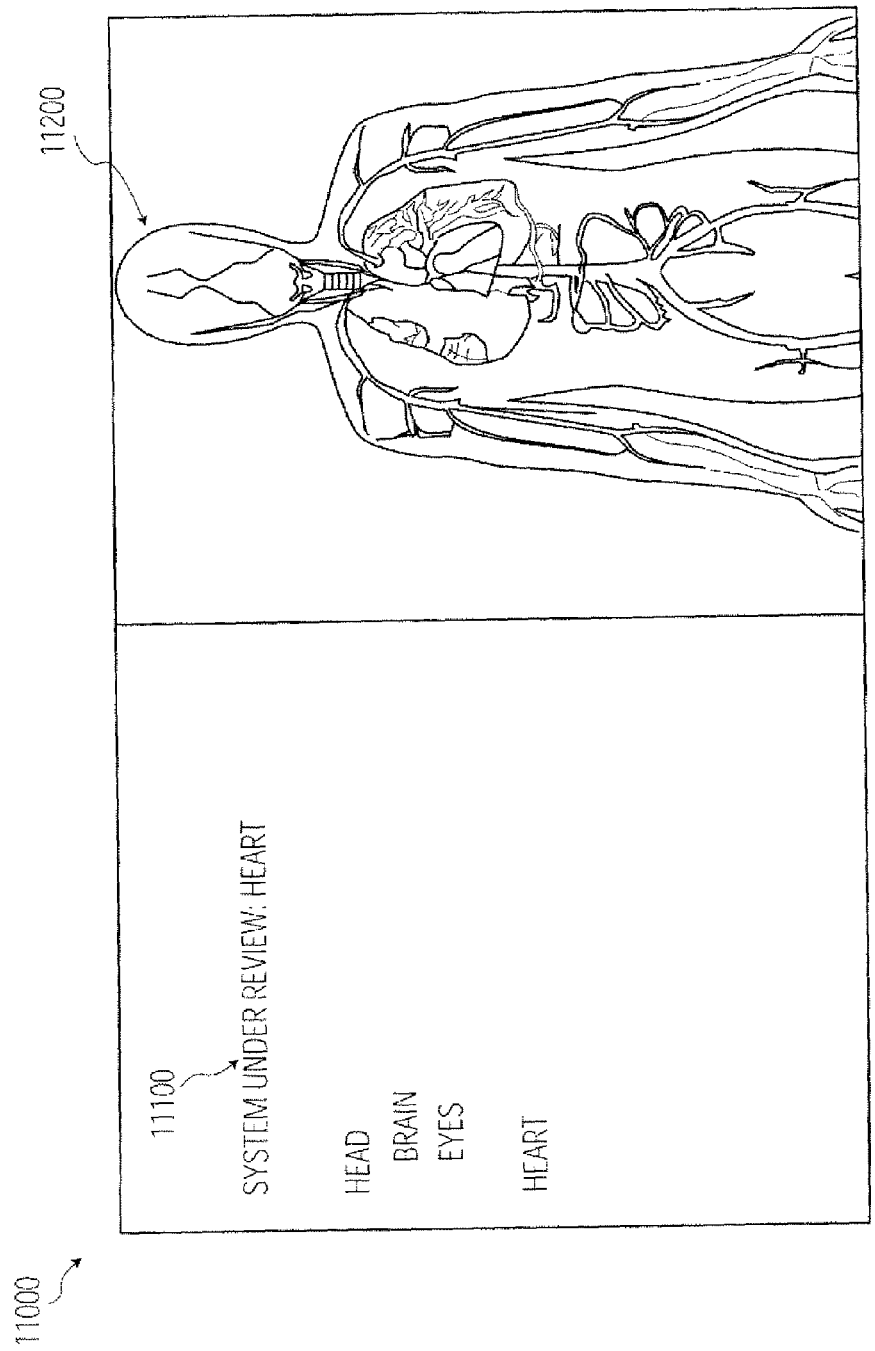
FIG. 11 is a diagram of an exemplary embodiment of a user interface 11000 of the present invention.

FIG. 11 is a diagram of an exemplary embodiment of a user interface 11000 of the present invention. User interface 11000 may display textual information 11100 and/or graphical information 11200, such as an image of an anatomical feature, for example, an image of a human body. Textual information 11100 may identify a navigation path through graphical information 11200, for example.

Figure 12:
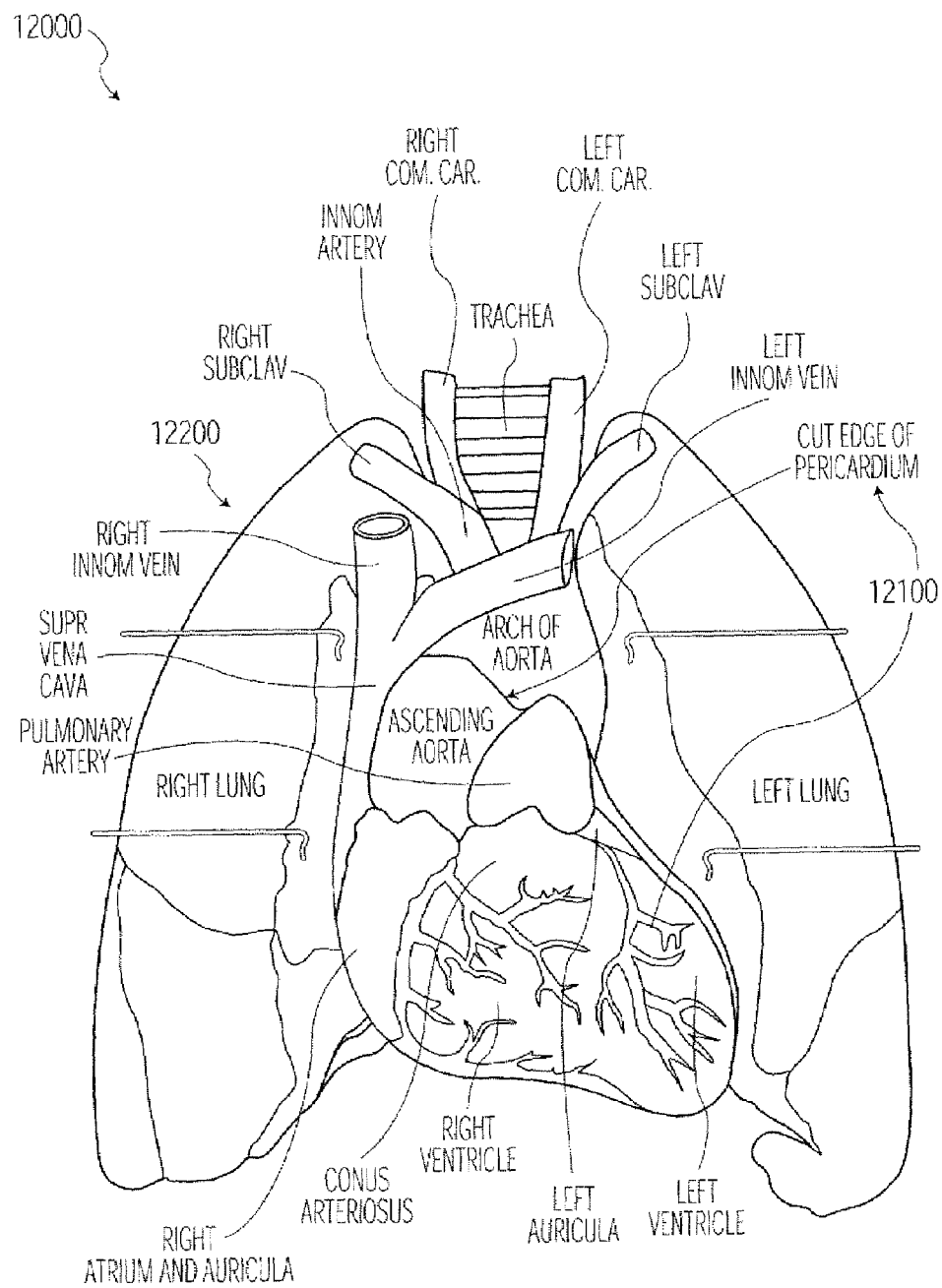
FIG. 12 is a diagram of an exemplary embodiment of a user interface 12000 of the present invention.

FIG. 12 is a diagram of an exemplary embodiment of a user interface 12000 of the present invention. User interface 12000 may display textual information 12100 that overlays and/or is linked to graphical information 12200. For example, user interface 12000 may provide a graphical image of a human heart 12200, areas of which may be labeled via descriptive textual information 12100. Any portion of graphical information 12200 (such as the left ventricle area) and/or textual information 12100 (such as the "left ventricle" label) may be hyperlinked to a detailed image and/or textual information corresponding to that particular portion.

Figure 13:
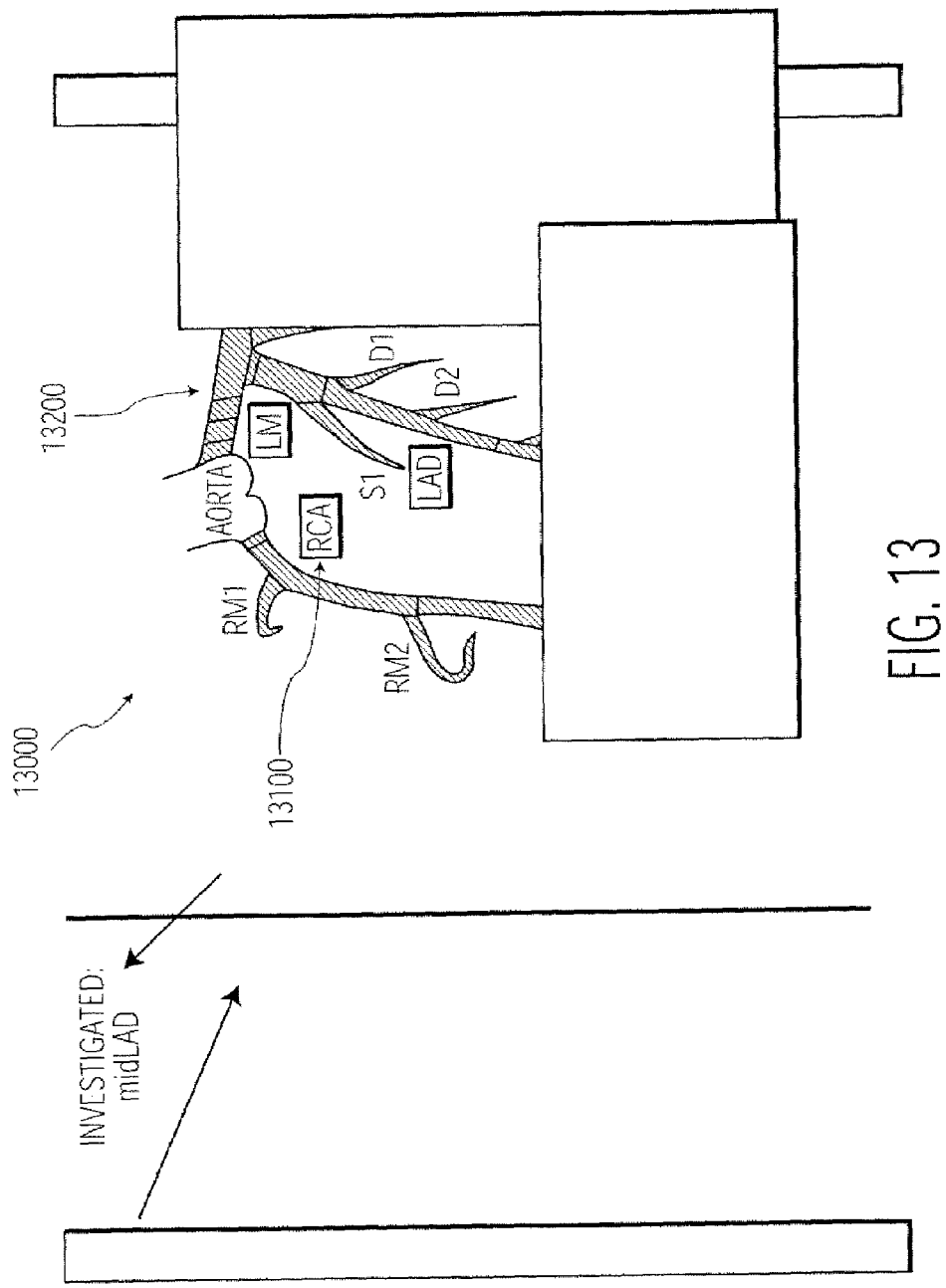
FIG. 13 is a diagram of an exemplary embodiment of a user interface 13000 of the present invention.

An example of such a detailed image and textual information is provided in FIG. 13, which is a diagram of an exemplary embodiment of a user interface 13000 of the present invention. User interface 13000 may include graphical information 13200, such as an image of at least a portion of an arterial system serving a human heart. In addition, user interface 13000 may include textual information 13100, such as textual labels of various components of that arterial system (such as, for example, the RCA (right common iliac artery), and the Cx (circumflex coronary artery)). Moreover, textual information 13100 may also include textual navigational and/or notational information.

Figure 14:
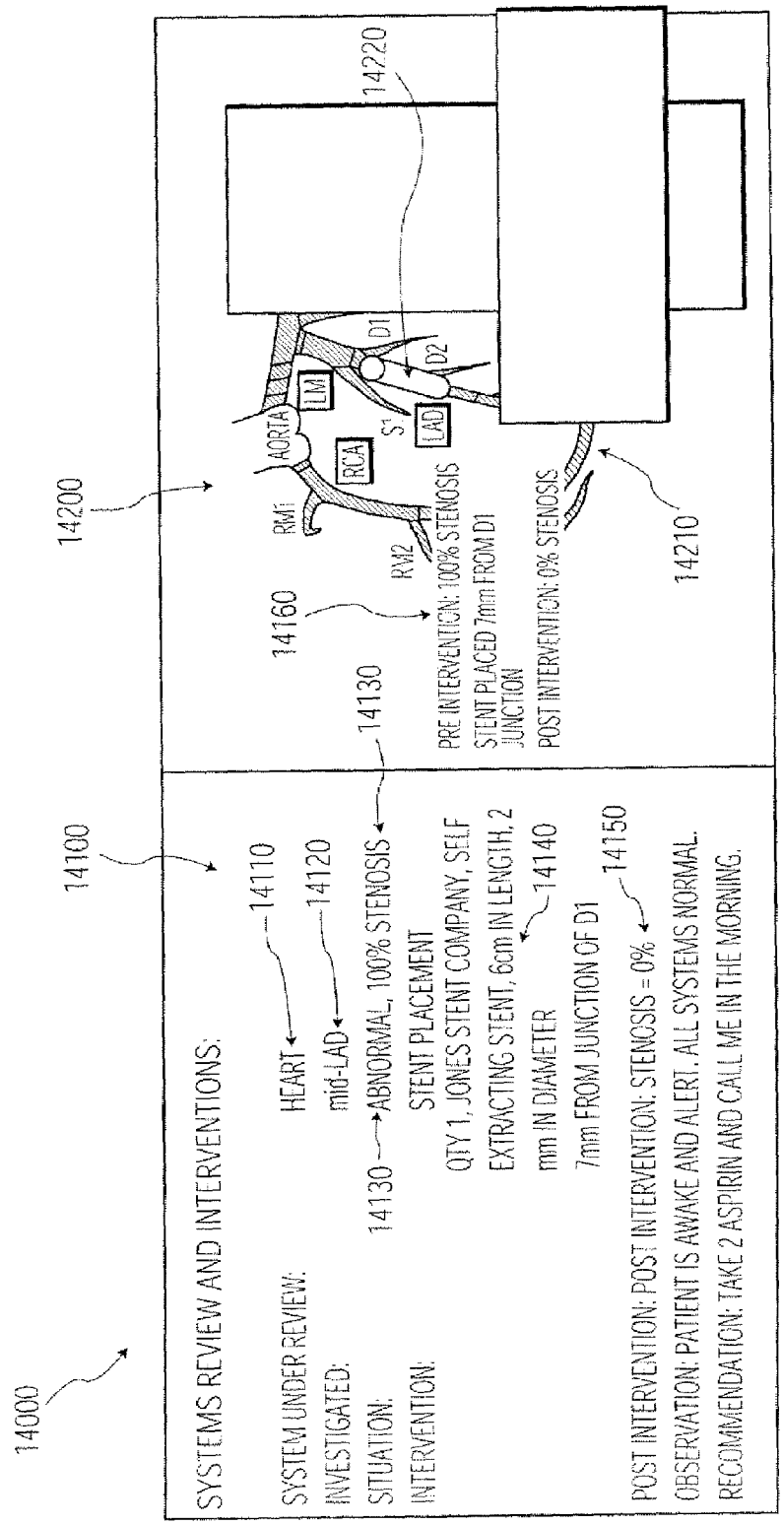
FIG. 14 is a diagram of an exemplary embodiment of a user interface 14000 of the present invention.

FIG. 14 is a diagram of an exemplary embodiment of a user interface 14000 of the present invention. User interface 14000 may display textual information 14100 and/or graphical information 14200. Textual information 14100 may communicate, for example, observations, notes, measurements, data, considerations, and/or recommendations regarding an anatomical component and/or feature 14110, an investigated aspect of that anatomical component and/or feature 14120, a diagnosis 14130, an intervention and/or treatment plan 14140, an inter-intervention and/or inter-treatment condition, a post-intervention and/or post-treatment situation 14150. Graphical information 14200 may comprise an image, such as an image of an anatomical component and/or feature of concern 14210, and may include additional graphical information, such as stent 14220, and/or textual information 14160.

Figure 15:
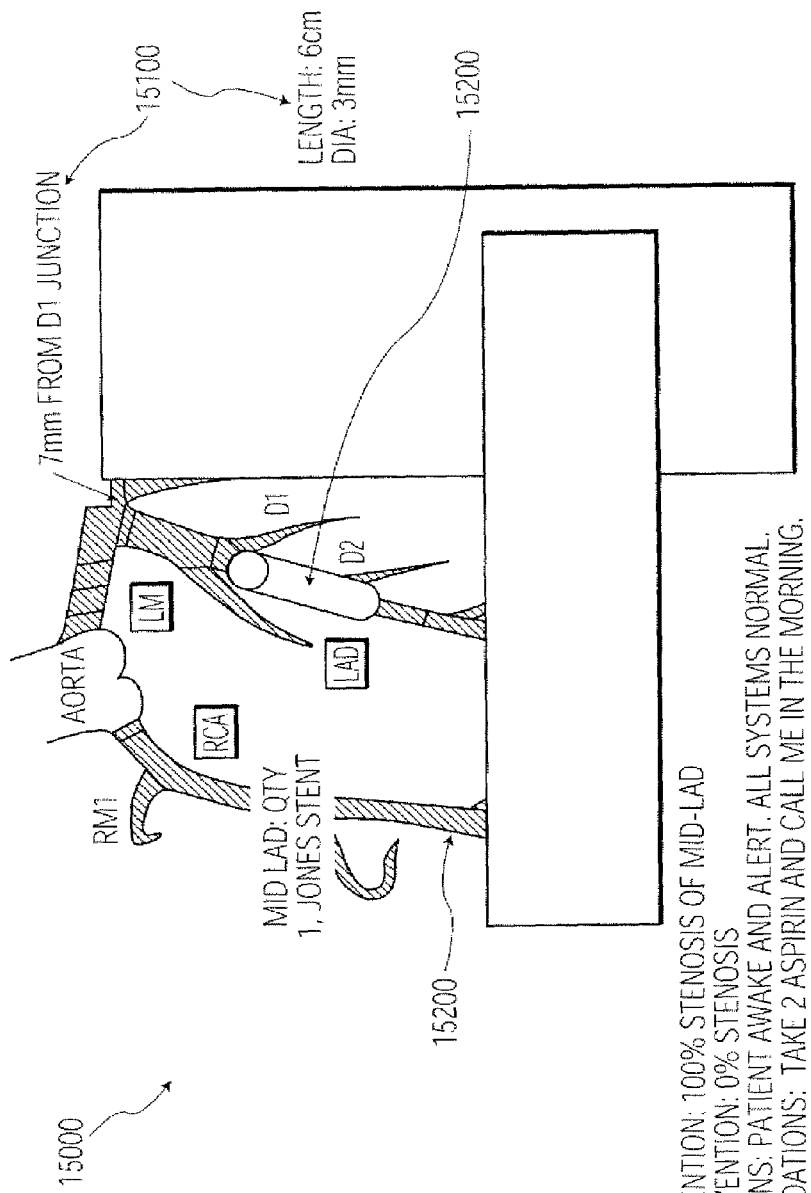
FIG. 15 is a diagram of an exemplary embodiment of a user interface 15000 of the present invention.

FIG. 15 is a diagram of an exemplary embodiment of a user interface 15000 of the present invention. User interface 15000 may display textual information 15100 and/or graphical information 15200. Textual information 15100 and/or graphical information 15200 may communicate, for example, observations, notes, measurements, data, considerations, and/or recommendations regarding an anatomical component and/or feature, an investigated aspect of that anatomical component and/or feature, a diagnosis, an intervention and/or treatment plan, an inter-intervention and/or inter-treatment condition, a post-intervention and/or post-treatment situation. Graphical information 15200 also may comprise an image, such as an image of an anatomical component and/or feature of concern, a surgical procedure, and/or medical device (such as a stent).

Although the invention has been described with reference to specific embodiments thereof, it will be understood that numerous variations, modifications and additional embodiments are possible, and accordingly, all such variations, modifications, and embodiments are to be regarded as being within the spirit and scope of the invention. Accordingly, the drawings and descriptions are to be regarded as illustrative in nature, and not as restrictive.

What is claimed is:

1. A method for creating an electronic form for soliciting information for use in healthcare management, comprising the activities of:
   initiating generation of at least one display image supporting a user in:
   selecting a template form for soliciting information, from a repository of template forms,
   modifying a data type of a data field within said selected template form to produce said electronic form for soliciting information for use in healthcare management by linking a user selected object chosen from a predetermined list of objects with a user selected data field of said selected template form, objects in said predetermined list being automatically derived and provided in response to at least one of, (a) a particular role of a healthcare worker and (b) a particular treatment activity being performed in providing healthcare to a patient, said selected object being usable in determining a query to be used in soliciting data for entry in said user selected data field and
   associating a name with said electronic form for soliciting information; and
   storing said electronic form in response to user command.

2. A method according to claim 1, wherein
   said query is for display in said user selected data field.

3. A method according to claim 1, wherein
   said at least one display image supports a user in creating said selected object by enabling a user to select a related object from said predetermined list and by at least one of, (a) selecting a data type for a created object, and (b) entering a name for said created object.

4. A method according to claim 3, further comprising the activity of:
   including said object name in said predetermined list.

5. A method according to claim 1, wherein said selected object supports categorizing data solicited for entry in said user selected data field.

6. A method according to claim 1, further comprising the activity of:
   in response to user selection of said modified form, associating said form with at least one of, (a) a particular patient and (b) a particular healthcare worker and
   pre-populating said modified form with data associated with at least one of, (i) said particular patient and (ii) said particular healthcare worker and
   said particular treatment activity is performed by a worker having a particular role in providing healthcare to a patient.

7. A method according to claim 1, further comprising the activity of:
   associating said query with said user selected data field.

8. A method according to claim 1, further comprising the activity of:
   rendering said query upon a user-caused event.

9. A method according to claim 1, further comprising the activity of:
   rendering said query upon entry of a cursor into said user selected data field.

10. A system embodied on a computer-readable media for implementing claim 1 wherein
    said activity of initiating generation of at least one display image is performed using a display processor and said display processor stores said modified form in said repository.

11. A graphical user interface, embodied on a computer-readable media, for creating an electronic form for soliciting information for use in healthcare management, said graphical user interface comprising:
  a graphical listing of a plurality of selectable template forms for soliciting information;
  a selected template form from the plurality of selectable template forms;
  a graphical linking element adapted to modify a data type of a data field within said selected template form by linking a user selected object from a predetermined list of objects with a user selected data field of said selected template form to produce said electronic form for soliciting information for use in healthcare management, objects in said predetermined list being automatically derived and provided in response to at least one of, (a) a particular role of a healthcare worker and (b) a particular treatment activity being performed by a worker having a particular role in providing healthcare to a patient, said selected object being usable in determining a query to be used in soliciting data for entry in said user selected data field; and
  a graphical rendering of a name associated with said electronic form for soliciting information.

12. A computer-readable media containing instructions for activities comprising:
  initiating generation of at least one display image supporting a user in,
  selecting a template form from a repository of template forms for soliciting information,
  modifying a data type of a data field within said selected template form to produce an electronic form for soliciting information for use in healthcare management by linking a user selected object chosen from a predetermined list of objects with a user selected data field of said selected template form, objects in said predetermined list being automatically derived and provided in response to at least one of, (a) a particular role of a healthcare worker and (b) a particular treatment activity being performed in providing healthcare to a patient, said selected object being usable in determining a query to be used in soliciting data for entry in said user selected data field and
  associating a name with said electronic form for soliciting information; and
  storing said electronic form in response to user command.

13. A method for scheduling a patient for receiving a particular service via at least one displayed image comprising an electronic template form, comprising the activities of:
  receiving patient identification information;
  initiating retrieval of said template form for use in scheduling a visit;
  automatically deriving a predetermined list of a available visit types in response to at least one of, (a) a particular role of a healthcare worker and (b) a particular treatment activity being performed in providing healthcare to a patient;
  automatically modifying a visit type data field in the retrieved template form by linking a particular patient visit type from the predetermined list of available visit types with a visit type data field;
  in response to user selection of a visit type data field in the modified template form, selecting a particular patient visit type from the predetermined list of available visit types linked with said visit type data field;
  in response to user selection of an appointment data field in the modified template form, selecting a particular visit appointment time and date from a predetermined list of available appointment times and dates linked with said appointment data field;
  in response to user selection of a service selection data field in the modified template form, selecting a particular service from a predetermined list of available services linked with said service selection data field;
  populating the modified template form with information comprising said patient identification information, said visit type, said appointment time and date and said particular service; and
  initiating scheduling of said visit by communicating the populated modified template form information to a recipient application in response to user command.

14. The method of claim 13, further comprising the activity of:
  receiving said list of available visit types and wherein said particular treatment activity is performed by a worker having a particular role in providing healthcare to a patient.

15. The method of claim 13, further comprising the activity of:
  linking said list of available visit types with said visit type data field.

16. The method of claim 13, further comprising the activity of:
  receiving said list of available appointment times and dates.

17. The method of claim 13, further comprising the activity of:
  linking said list of available appointment times and dates with said appointment data field.

18. The method of claim 13, further comprising the activity of: receiving said list of available services.

19. The method of claim 13, further comprising the activity of:
  linking said list of available services with said service selection data field, said list of available services being indicated in an automatically provided predetermined list derived in response to at least one of, (a) a particular role of a healthcare worker and (b) a particular treatment activity being performed in providing healthcare to a patient.

20. The method of claim 13, further comprising the activity of:
  creating said scheduling form.

21. A system embodied on a computer-readable media for implementing claim 13, wherein said activity of initiating retrieval of a template form is performed using a display processor and said display processor stores said modified form in said repository.

22. A graphical user interface, embodied on a computer-readable media, for scheduling a patient for receiving a particular service via at least one displayed image, comprising:
  a processor for automatically modifying a visit type data field in an electronic form by linking a particular patient visit type from the predetermined list of available visit types with a visit type data field in response to user selection of a particular patient visit type;
  a graphical and user-selectable visit type data field in the electronic form for selecting a particular patient visit type from a predetermined list of available visit types linked with said visit type data field, said predetermined list of available visit types being automatically derived and provided in response to at least one of, (a) a particular role of a healthcare worker and (b) a particular treatment activity being performed in providing healthcare to a patient;

a graphical and user-selectable appointment data field in the electronic form for selecting a particular visit appointment time and date from a predetermined list of available appointment times and dates linked with said appointment data field;

a graphical and user-selectable service selection data field in the electronic form for selecting a particular service from a predetermined list of available services linked with said service selection data field; and a processor for populating the electronic form with said patient identification information, said visit type, said appointment time and date, and said particular service.

23. A computer-readable media containing instructions for activities comprising:

receiving patient identification information;

initiating retrieval of a template form for use in scheduling a visit;

automatically deriving a predetermined list of available visit types in response to at least one of, (a) a particular role of a healthcare worker and (b) a particular treatment activity being performed in providing healthcare to a patient;

automatically modifying a visit type data field in the retrieved template form by linking a particular patient visit type from the predetermined list of available visit types with a visit type data field;

in response to user selection of a visit type data field in the modified template form, selecting a particular patient visit type from the predetermined list of available visit types linked with said visit type data field;

in response to user selection of an appointment data field in the modified template form, selecting a particular visit appointment time and date from a predetermined list of available appointment times and dates linked with said appointment data field;

in response to user selection of a service selection data field in the modified template form, selecting a particular service from a predetermined list of available services linked with said service selection data field;

populating the modified template with said patient identification information, said visit type, said appointment time and date and said particular service; and initiating scheduling of said visit by communicating the populated modified template form information to a recipient application in response to user command.

24. A method for creating an electronic healthcare management form for soliciting information comprising the activities of:

initiating generation of at least one display image supporting a user in, loading an image file into an electronic form file, the image file corresponding to a scanned healthcare management form for soliciting information;

modifying a data type of a data field within said scanned healthcare management form by designating a plurality of regions of the electronic form file as a plurality of form objects, each of the plurality of form objects associated with a data solicitation query;

for each form object from the plurality of form objects, associating the form object with one of a predetermined list of database fields, form objects in said predetermined list being automatically derived and provided in response to at least one of (a) a particular role of a healthcare worker and (b) a particular patient healthcare treatment activity; and storing the electronic form file.

* * * * *

UNITED STATES PATENT AND TRADEMARK OFFICE
CERTIFICATE OF CORRECTION

PATENT NO.      : 7,590,932 B2                              Page 1 of 1
APPLICATION NO. : 10/383324
DATED           : September 15, 2009
INVENTOR(S)     : Britton et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1356 days.

Signed and Sealed this

Twenty-first Day of September, 2010

David J. Kappos
*Director of the United States Patent and Trademark Office*